United States Patent
Yang et al.

(10) Patent No.: US 11,238,150 B2
(45) Date of Patent: Feb. 1, 2022

(54) DATA ENCRYPTION IN MEDICAL DEVICES WITH LIMITED COMPUTATIONAL CAPABILITY

(71) Applicant: AMGEN INC., Thousand Oaks, CA (US)

(72) Inventors: Huaying Yang, Vernon Hills, IL (US); Andrew Dean, San Diego, CA (US); Ferry Tamtoro, San Ramon, CA (US); Keng-Tong See, Camarillo, CA (US); Michael Friedman, Newbury Park, CA (US); Desheng Yin, Thousand Oaks, CA (US); Huixing Jin, Moorpark, CA (US); Edward Nielsen, Castaic, CA (US)

(73) Assignee: AMGEN INC., Thousand Oaks, CA (US)

( * ) Notice: Subject to any disclaimer, the term of this patent is extended or adjusted under 35 U.S.C. 154(b) by 568 days.

(21) Appl. No.: 16/300,705

(22) PCT Filed: May 16, 2017

(86) PCT No.: PCT/US2017/032820
§ 371 (c)(1),
(2) Date: Nov. 12, 2018

(87) PCT Pub. No.: WO2017/200989
PCT Pub. Date: Nov. 23, 2017

(65) Prior Publication Data
US 2020/0322793 A1    Oct. 8, 2020

Related U.S. Application Data
(60) Provisional application No. 62/337,029, filed on May 16, 2016.

(51) Int. Cl.
*H04K 1/00* (2006.01)
*G06F 21/44* (2013.01)
(Continued)

(52) U.S. Cl.
CPC ........ *G06F 21/445* (2013.01); *G06F 21/6245* (2013.01); *G16H 20/17* (2018.01);
(Continued)

(58) Field of Classification Search
CPC .................. G06F 21/445; G06F 21/44; H04W 12/00512; H04W 12/00; H04L 9/0866; H04L 63/061
(Continued)

(56) References Cited

U.S. PATENT DOCUMENTS

2001/0027331 A1* 10/2001 Thompson ............. G16H 40/40
607/60
2009/0043362 A1*  2/2009 Healy ................ A61N 1/37254
607/60
(Continued)

OTHER PUBLICATIONS

International Search Report for Application No. PCT/US2017/032820, dated Aug. 21, 2017.
(Continued)

*Primary Examiner* — Jeffrey C Pwu
*Assistant Examiner* — Samuel Ambaye
(74) *Attorney, Agent, or Firm* — Marshall, Gerstein & Borun LLP

(57) ABSTRACT

A medical device with limited computational capability includes medical hardware, a first register to store a static, substantially unique identifier of the medical device, a second register to store a static encryption key, an interface to receive and transmit data over a short-range communication link, and processing hardware. The processing hardware is configured to apply the static encryption key to the
(Continued)

identifier of the medical device to generate an encrypted identifier, transmit the encrypted identifier of to another device via the interface, receive an encrypted identifier of the other device, decrypt the encrypted identifier of the other device using the static encryption key to determine an identifier of the other device, generate a dynamic encryption key using the identifier of the medical device and the identifier of the other device, and apply the dynamic encryption key to medical data transmitted between the medical device and the other device.

20 Claims, 5 Drawing Sheets

(51) Int. Cl.
| | |
|---|---|
| G16H 20/17 | (2018.01) |
| G16H 40/40 | (2018.01) |
| G06F 21/62 | (2013.01) |
| H04L 9/08 | (2006.01) |
| H04L 9/14 | (2006.01) |
| H04L 29/06 | (2006.01) |
| G16H 40/67 | (2018.01) |
| H04W 12/03 | (2021.01) |
| H04W 12/50 | (2021.01) |
| H04W 12/71 | (2021.01) |

(52) U.S. Cl.
CPC ............ *G16H 40/40* (2018.01); *G16H 40/67* (2018.01); *H04L 9/0866* (2013.01); *H04L 9/0869* (2013.01); *H04L 9/14* (2013.01); *H04L 63/061* (2013.01); *H04L 63/0876* (2013.01); *H04W 12/03* (2021.01); *H04W 12/50* (2021.01); *H04W 12/71* (2021.01); *G06F 2221/2107* (2013.01); *G06F 2221/2141* (2013.01); *H04L 2209/12* (2013.01); *H04L 2209/805* (2013.01); *H04L 2209/88* (2013.01)

(58) Field of Classification Search
USPC ......................................................... 380/270
See application file for complete search history.

(56) References Cited

U.S. PATENT DOCUMENTS

| | | | |
|---|---|---|---|
| 2010/0115286 A1* | 5/2010 | Hawkes | ................ H04L 9/0618 |
| | | | 713/189 |
| 2011/0029778 A1 | 2/2011 | Garcia Morchon et al. | |
| 2011/0302414 A1* | 12/2011 | Logan | .................... H04L 51/02 |
| | | | 713/168 |

OTHER PUBLICATIONS

Written Opinion of the International Searching Authority for Application No. PCT/US2017/032820, dated Aug. 21, 2017.

* cited by examiner

DATA ENCRYPTION IN MEDICAL DEVICES WITH LIMITED COMPUTATIONAL CAPABILITY

CROSS-REFERENCE TO RELATED APPLICATION

This application is a United States national phase of International Patent Application No. PCT/US2017/032820, having an international filing date of May 16, 2017, which claims the priority benefit of U.S. Provisional Patent Application No. 62/337,029, filed May 16, 2016. The entire contents thereof of International Patent Application No. PCT/US2017/032820 and U.S. Provisional Patent Application No. 62/337,029 are hereby incorporated herein by reference for all purposes.

FIELD OF DISCLOSURE

The present disclosure generally relates to medical devices with limited computational capability that securely exchange data with other medical devices or general-purpose computing devices and, more particularly, to efficiently encrypting data transmitted to and from such medical devices.

BACKGROUND

Certain medical devices can wirelessly transmit data to, and receive data from, other computing devices. While some of these medical devices are equipped with powerful processors and operate using a permanent power supply, other medical devices are designed to operate using little power and/or have limited computational capabilities. In some cases, these low-power and/or low-computation devices may transmit and/or receive sensitive data, including, for example, a patient's private medical information. However, it is difficult to protect this data from interception and tampering due to the inability of such medical devices to effectively generate encryption keys and, more generally, run encryption or decryption.

Drug delivery devices are a class of medical devices for which it has become increasingly common to incorporate wireless communication capabilities. Drug delivery devices encompass a wide variety of devices including, but not limited to, syringes, autoinjectors, on-body injectors, transdermal patches, ambulatory infusion pumps, and implantable infusion pumps. The use of drug delivery devices has become more widespread in recent years, in part, due to the growth in injectable drugs such as biologics, and also because of an increased demand for drugs administrable in large volume doses.

Many conventional drug delivery devices, such as syringes, were designed for use by medically-trained personnel, and therefore were difficult for laypersons to operate. More recently, however, drug delivery devices, including autoinjectors and on-body injectors, have begun to incorporate automated and/or simplified features, so that the device can be used by a patient to self-administer a drug with little or no assistance from a caregiver.

The trend to automate drug delivery devices has led to the incorporation of various onboard electronic and software-implemented features, including sensors for collecting and reporting data related to the device or patient, as well as features enabling the remote control of the drug delivery device. Such features tend to require and/or benefit from the drug delivery device communicating data with one or more remote computing devices. A risk inherent to communicating data is that of interception by a malicious third party. Interception is particularly problematic in the context medical devices because the intercepted data may include private details about the patient's medical history and/or other sensitive information. Furthermore, if the third party tampers or otherwise modifies the intercepted data, untimely and/or improper operation of the drug delivery device could result.

Many drug delivery devices are designed to be disposable and/or low cost, and therefore do not possess the power and/or computational capabilities necessary to execute conventional data security algorithms for protecting wireless communications. Accordingly, methods and systems are needed that can be implemented by drug delivery devices and other medical devices with limited computational capabilities to provide secure wireless communications, and that may address one or more of other needs or challenges described herein.

SUMMARY

Disclosed herein are techniques for generating a dynamic encryption key for use by a medical device, using little computation and without requiring a connection to a wide area network such as the Internet. These techniques include encrypting a unique device using a shared static encryption key and exchanging the encrypted device identifiers between devices to set up a multi-factor dynamic key. These techniques also include encrypting and decrypting data using the dynamic key.

One example embodiment of these techniques is a medical device with limited computational capability. The medical device includes medical hardware configured to perform a medical function on a human or animal body, such as delivering a drug. The medical device also includes a first register to store a static, substantially unique identifier of the medical device and a second register to store a static encryption key. Further, the medical device includes an interface to receive and transmit data over a short-range communication link. Still further, the medical device includes processing hardware communicatively coupled to the first register, the second register, the interface and the medical hardware, and configured to: (i) apply the static encryption key to the identifier of the medical device to generate an encrypted identifier of the medical device, (ii) transmit, via the interface, the encrypted identifier of the medical device to another device, (iii) receive, via the interface, an encrypted identifier of the other device, (iv) decrypt the encrypted identifier of the other device using the static encryption key to determine an identifier of the other device, (v) generate a dynamic encryption key using the identifier of the medical device and the identifier of the other device, and (vi) apply the dynamic encryption key to medical data transmitted between the medical device and the other device, where the medical data is related to operation of the medical hardware.

Another example embodiment is a system comprising a first device and a second device. The first device includes medical hardware configured to perform a medical function and generate medical data related to the medical function, an interface to receive and transmit data over a short-range communication link, and processing hardware configured to generate a dynamic encryption key, encrypt the medical data using the dynamic encryption key, and transmit the encrypted medical data via the short-range communication link. The second device includes an interface to receive and transmit data over the short-range communication link, and processing hardware configured to generate the dynamic encryption key, receive the encrypted medical data via the short-range communication link, and decrypt the medical data using the dynamic encryption key. Each of the first device and the second device stores a shared static encryption key and a respective different device identifier. Further, each of the first device and the second device generates the dynamic encryption key using the shared static encryption key and the device identifiers of the first device and the second device.

Still another embodiment of these techniques is a method for generating dynamic encryption keys in medical devices. The method includes retrieving, by processing hardware, an identifier of a medical device and a pre-stored static key and receiving, via a wireless communication link, an encrypted identifier of a peer device. The method further includes decrypting the encrypted identifier using the pre-stored static key to determine an identifier of the peer device and generating a dynamic encryption key using the identifier of a medical device and the identifier of the peer device. Still further, the method includes performing a medical function by medical hardware, the medical function being associated with medical data, and exchanging the medical data with the peer device via the wireless communication link, including applying the dynamic encryption key to the medical data.

BRIEF DESCRIPTION OF THE DRAWINGS

Same reference numerals are used in the drawings to identify same or similar elements and structures in the various embodiments.

DETAILED DESCRIPTION

Figure 1:
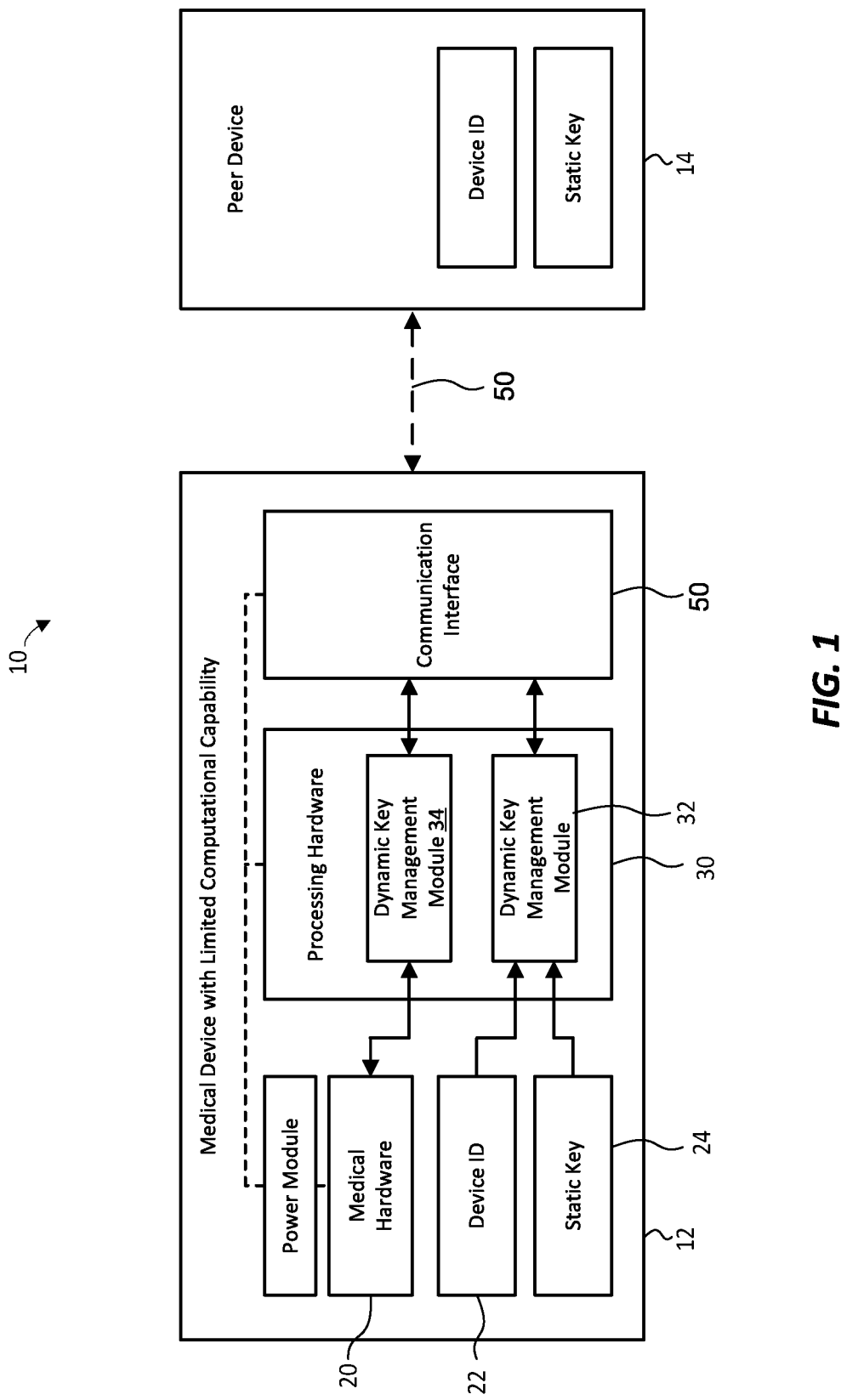
FIG. 1 is a block diagram of an example communication system in which a medical device generates a dynamic encryption key for securely exchanging data with another device, in accordance with the techniques of the present disclosure.

FIG. 1 is a block diagram of an example computing system 10 in which the dynamic encryption key generation techniques of this disclosure can be implemented. The system 10 includes a medical device 12 and a peer device 14, which can be another medical device, a remote control device, a communication device such as a smartphone, or another computing device such as a laptop computer. In general, the medical device 12 and the peer device 14 implement a minimal computation multi-factor (MCMF) scheme for generating a dynamic encryption key that is based on the respective device identifiers. Using this technique, the medical device 12 spends little power and few computing operations to obtain a dynamic encryption key. Moreover, the MCMF scheme does not require that the medical device 12 be able to access a wide area network such as the Internet. Accordingly, the techniques of the present disclosure enable secure communications without substantially increasing the data processing load and/or power requirements of a medical device. Moreover, because the presently-disclosed communication techniques do not require the medical device to incorporate costly and/or complex processing hardware, they may be suitable for a wide variety of medical devices, including ones that are low-cost and/or disposable such as certain autoinjectors and on-body injectors.

In an example embodiment, the medical device 12 includes a medical hardware module 20, a register 22 that stores a substantially unique identifier of the medical device 12, another register 24 that stores a static encryption key, a power module 26, processing hardware 30, and a communication interface module 40. The processing hardware 30 in this embodiment includes a dynamic key management module 32 and an encryption/decryption module 34.

The medical device 12 may be, for example, an autoinjector prescribed to a patient for self-administering drug or other medicament. Accordingly, the medical hardware 20 of the medical device 12 may include a mechanism that drives a needle and/or a plunger of a syringe in order to subcutaneously deliver a drug (none of which are shown in FIG. 1 to avoid visual clutter). The syringe may be pre-filled with the drug and may operate in response to a triggering event, such as the patient pressing a button on the device. For example, the mechanism may drive the needle into the patient and advance the plunger to deliver the drug subcutaneously via the needle.

In some embodiments, the medical device 12 may be configured as an on-body injector attachable to a patient's body tissue (e.g., skin, organ, muscle, etc.) and capable of automatically delivering a subcutaneous injection of a fixed or patient-selected dose of a drug over a controlled or selected period of time. In such embodiments, the medical hardware 20 of the medical device 12 may include, for example, an adhesive or other means for temporarily attaching the on-body injector to the patient's body tissue, a primary container for storing a drug or medicament, a drive mechanism configured to drive or permit the release of a plunger to discharge the drug from the primary container, a trocar (e.g., a solid core needle), a flexible cannula disposed around the trocar, an insertion mechanism configured to insert the trocar and/or flexible cannula into the patient and optionally retract the trocar leaving the flexible cannula in the patient, a fluid pathway connector configured to establish fluid communication between the primary container and the flexible cannula upon device activation, and an actuator (e.g., a user displaceable button) configured to activate the device (none of which are shown in FIG. 1 to avoid visual clutter). In some embodiments, the on-body injector may be pre-filled and/or pre-loaded.

Furthermore, the medical hardware 20 of the medical device 12 may be similar to, or the same as, the hardware of one or more of the autoinjectors, on-body injectors, and other drug delivery devices described in any of the following documents, each of which is incorporated by reference in its entirety for all purposes: U.S. Provisional Patent Application No. 62/275,491 entitled "AUTO-INJECTOR WITH SIGNALING ELECTRONICS"; U.S. Provisional Patent Application No. 62/266,788 entitled "SMART PACKAGING FOR DRUG DELIVERY DEVICES"; U.S. Provisional Patent Application No. 62/265,142 entitled "AUTO-INJECTOR WITH SIGNALING CAP"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE" U.S. Patent Application Publication No. 2014/0288511; U.S. Patent Application Publication No. 2015/0374919; U.S. Patent Application Publication No. 2015/0290390; U.S. Patent Application Publication No. 2015/0374919; U.S. Pat. No. 9,061,097; International Patent Application No. PCT/US15/29485 entitled "AUTOINJECTOR WITH SCHOCK REDUCING ELEMENTS"; International Patent Application No. PCT/US15/64869 entitled "DRUG DELIVERY DEVICE WITH LIVE BUTTON OR USER INTERFACE FIELD"; International Patent Application No. PCT/US2016/018149 entitled "DRUG DELIVERY DEVICE WITH VACUUM ASSISTED SECUREMENT AND/OR FEEDBACK"; International Patent Application Publication No. PCT/US2015/066597 entitled "DRUG DELIVERY DEVICE WITH PROXIMITY SENSOR"; International Patent Application Publication No. WO/2015/187805; International Patent Application Publication No. WO/2015/187797; International Patent Application Publication No. WO/2015/187799; International Patent Application Publication No. WO/2015/187802; International Patent Application Publication No. WO/2015/187805; International Patent Application Publication No. WO/2016/003813; International Patent Application Publication No. WO/2015/061389; International Patent Application Publication No. WO/2014/081780; International Patent Application Publication No. WO/2015/119906; International Patent Application Publication No. WO/2015/061386; International Patent Application Publication No. WO/2016/061220; International Patent Application No. PCT/US2017/17627 entitled "DRUG DELIVERY DEVICE, METHOD OF MANUFACTURE, AND METHOD OF USE"; International Patent Application No. PCT/US2017/26524 entitled "DRUG DELIVERY DEVICE, METHOD OF MANUFACTURE, AND METHOD OF USE"; U.S. Provisional Patent Application No. 62/329,255 entitled "DRUG DELIVERY DEVICE WITH MESSAGING LABEL"; U.S. Provisional Patent Application No. 62/376,004 entitled "DRUG DELIVERY DEVICE WITH PLACEMENT DETECTION"; U.S. Provisional Patent Application No. 62/275,491 entitled "AUTO-INJECTOR WITH SIGNALING ELECTRONICS"; U.S. Provisional Patent Application No. 62/365,185 entitled "AUTOINJECTOR WITH LEAD SCREW AND PLANETARY GEAR COUPLER POWER PACK"; U.S. Provisional Patent Application No. 62/357,713 entitled "DRUG DELIVERY DEVICE HAVING MINIMIZED RISK OF COMPONENT FRACTURE UPON IMPACT EVENTS"; U.S. Provisional Patent Application No. 62/447,174 entitled "INJECTION DEVICES AND RELATED METHODS OF USE AND ASSEMBLY"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/412,365 entitled "ON-BODY INJECTOR"; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; and U.S. Provisional Patent Application No. 62/468,190 entitled "INSERTION MECHANISM AND METHOD OF INSERTING A NEEDLE OF A DRUG DELIVERY DEVICE".

In additional to mechanical components, the medical hardware 20 may include electric and/or electronic components. For example, an electronic switch may be coupled to the mechanism for driving the needle. The medical device 12 may receive an encrypted signal, decrypt the signal using the techniques of this disclosure, determine that the signal includes a command to operate the switch, and cause the switch to drive the needle and deliver the drug. Thus, the medical device 12 in this embodiment is configured to perform a medical function using the medical hardware 20 in response to a remote command.

In another embodiment, the medical hardware 20 includes a travel sensor and an analog-to-digital (A/D) converter to generate a digital signal indicative of the distance traveled by the needle or plunger. Upon delivering the medicament, the medical device 12 may obtain a reading from the sensor, encrypt the reading using the techniques of this disclosure, and securely report the reading to the peer device 14. Additionally or alternatively, the medical device 12 may report other measurements or parameters to the peer device 14, such as a time at which the medicament was delivered. In these embodiments, the medical device 12 is configured to provide data related to the operation of the medical hardware 20 to a remote device.

Further, the medical device 12 in some embodiments both receives encrypted data from the peer device 14 and transmits encrypted data to the peer device 14. More generally, the medical hardware 20 of the medical device 12 may implement any suitable one or several medical functions and may include one or more sensors. Such sensor(s) can be configured to detect an operational state of the medical device 12 (e.g., unpackaged/ready for administration, sterile barrier removal, contact with patient's body tissue, cannula and/or needle insertion, drug delivery initiation, actuator or button displacement, drug delivery completion, plunger position, fluid pathway occlusion, etc.), a condition of the medical device 12 or drug contained therein (e.g., temperature, shock or vibration exposure, light exposure, drug color, drug turbidity, drug viscosity, geographic location, spatial orientation, temporal information, ambient air pressure, etc.), and/or physiological information about the patient (e.g., body temperature, blood pressure, pulse or heart rate, glucose levels, physical activity or movement, fingerprint detection, etc.).

The medical device 12 may be constructed as single-use (i.e., disposable) or reusable device. Further, the medical device 12 may be wearable. In either case, however, the medical device 12 may have only limited computational capability, and the power module 26 (which can be a small battery, for example) may store only a relatively small charge. In at least some of the embodiments, the medical device 12 is designed as an inexpensive device with a relatively short life span, and without wide-area network communication capability.

With continued reference to FIG. 1, the register 22 can be any suitable data storage unit, which can be implemented as read-only memory (ROM) that stores a sequence of numbers or alphanumeric characters, for example. The device identifier can conform to any suitable format such as Unique Device Identification (UDI) specified by the Food and Drug Administration of the United States.

The register 24 also may be implemented as a read-only memory module and can store a static key of any suitable length. In at least one embodiment, the registers 22 and 24 are implemented as portions of a same memory module. The length and, accordingly, the strength of the static key may be selected in accordance to the type of data communicated between the devices 12 and 14 and/or the length of the device identifier stored in the register 22. In general, using longer static and dynamic keys increases the strength of encryption but requires longer computation. The value of the static key for storage in the register 24 may be specified at compile time.

In at least one embodiment, the processing hardware 30 is implemented as dedicated circuitry or logic that is permanently configured to execute specifically the limited set of functions of the medical device 12. To this end, the processing hardware 30 may be implemented as a special-purpose processor, such as a field programmable gate array (FPGA) or an application-specific integrated circuit (ASIC). In another embodiment, the processing hardware 30 includes a general-purpose processor (e.g., a CPU) or another programmable processor that is temporarily configured by software to execute the functions of the medical device 12. More generally, the processing hardware 30 may be implemented using hardware, firmware, software, or a suitable combination of hardware, firmware, and software. In any case, however, the processing hardware 30 may be limited by one or more factors including computational capability, power capacity, memory capacity, availability of a network connection, etc. For example, the processing hardware 30 implemented using FPGA or ASIC may not include the functionality of a random number generator and, as a result, the processing hardware 30 cannot perform certain encryption techniques. Further, the medical device 12 may not have access to a wide area network, and thus certain techniques for obtaining static and/or dynamic encryption techniques may not be available to the processing hardware 30.

Referring still to FIG. 1, the dynamic key management module 32 may generate a dynamic key using the device identifier stored in the register 22, the device identifier received from the peer device 14, and the static key stored in the register 24. The encryption/decryption module 34 then may apply the dynamic key to outbound data generated by the medical hardware 20 and/or the inbound data received via the communication interface 40. The dynamic key thus may be unique to a pair of communicating devices, as long as the corresponding device identifiers are sufficiently unique, subject to small probability of collision between pairs of identifiers when bitwise XOR is used, for example. The techniques implemented by the modules 32, 34 or similar components are discussed in more detail below with reference to FIGS. 3 and 4.

In at least one embodiment, the encryption/decryption module 34 implements a symmetric encryption algorithm, so that the same dynamic key can encrypt outbound data and decrypt inbound data. The symmetric encryption algorithm may correspond to any suitable stream cipher or block cipher techniques, including those known in the art (e.g., DES, AES, Serpent, Twofish). In at least one embodiment, the encryption/decryption module 34 implements a simplified algorithm to reduce computation time, such as S-DES.

As illustrated in FIG. 1, the processing hardware 30 may be communicatively coupled to the communication interface 40, which may be implemented any suitable short-range communication scheme such as a personal area network according to IEEE 802.15 protocols (e.g., Bluetooth®, Zig-Bee) or IEEE 802.11 protocols (e.g., Wi-Fi™), infrared communications according to the Infrared Data Association standards (IrDA), etc. Depending on the embodiment, the communication interface 40 may transmit data to the peer device 14, from the peer device 14, or both to and from the peer device 14 via a wireless communication link 50.

Similar to the medical device 12, the peer device 14 may store a device identifier 52 and a copy 54 of the static encryption key. In at least one embodiment, the device identifier 54 conforms to the same format as the device identifier stored in the register 22 of the medical device 12. In another embodiment, however, the device identifier is shorter or longer than the device identifier of the medical device 12, and the peer device 14 or the medical device 12 uses only the symbols or bits of one of the device identifiers. For example, if the device identifier of the medical device 12 is 10 bytes long while device identifier of the peer device 14 is 12 bytes long, the devices 12 and 14 can utilize only the last 10 bytes of the device identifier of the peer device 14 when generating a dynamic encryption key.

In general, the peer device 14 may be another medical device, a remote control device, a communication device such as a smartphone, a laptop computer, a desktop computer, a tablet computer, a smartwatch, etc. It is noted that the term "peer device" here is used to reference to the communication mode between the devices 12 and 14. In some cases, the peer device 14 has limited computational capability and power restrictions similar to the medical device 12. In other cases, however, the peer device 14 has more processing power, but the peer device 14 symmetrically supports the communication scheme of the medical device 12. Further, the peer device 14 in some embodiments is configured to communicate with a remote server via a wide area network. In one such example embodiment, the medical device 12 reports successful delivery of the medicament to the peer device 14, and the peer device 14 in turn reports the timing of the delivery of the medicament via a wide area network to a remote server that monitors the patient's compliance with a prescribed treatment regimen.

Figure 2:
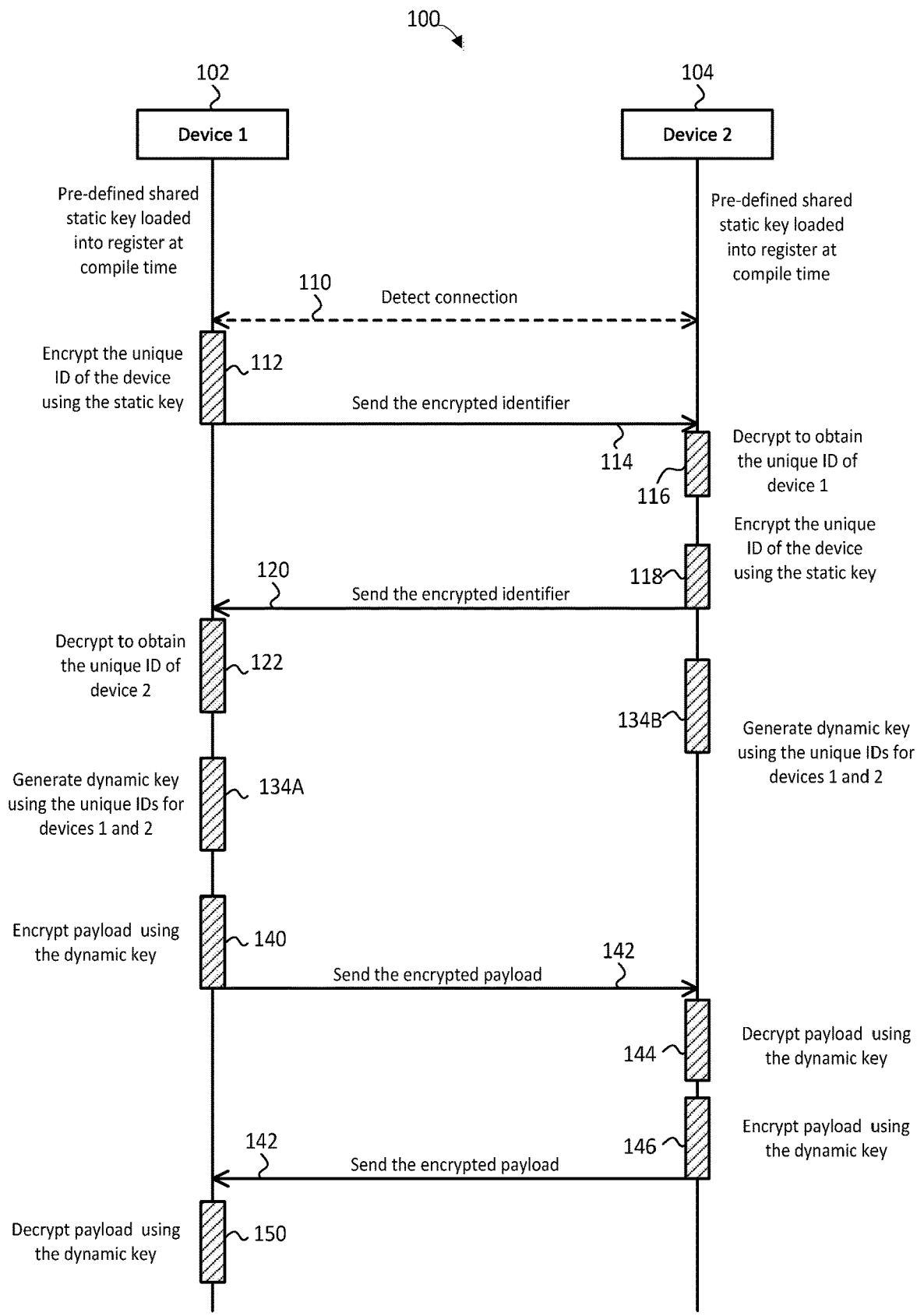
FIG. 2 is a message sequence diagram of an example secure exchange of data between two devices using a dynamic encryption key, where the dynamic encryption key is generated using the techniques of the present disclosure.

Now referring to FIG. 2, a message sequence diagram 100 illustrates an example exchange of data between a pair of devices 102 and 104, which may correspond to the medical device 12 and the peer device 14, respectively. As discussed below, the devices 102 and 104 may exchange encrypted device identifiers to set up a dynamic key during the first encryption stage. During the second encryption stage, the devices 102 and 104 may encrypt data payloads using the dynamic key.

In particular, the device 102 and/or the device 104 may detect the proximity of the other one of the devices 102 and 104 and attempt to automatically set up a communication link (event 110). Each of the devices 102 and 104 may store a pre-defined static encryption key, which may be loaded into the corresponding memory at compile time. Similarly, each of the devices 102 and 104 may store a respective device identifier, in the same format or different formats reducible to a single format.

In response to the event 110, the device 102 may encrypt the unique identifier of the device 102 using the static encryption key (event 112) and send the encrypted identifier to the device 104 (event 114). The identifier of the device 102 thus may travel via a wireless communication link in an encrypted format rather than in an unprotected format. Upon receiving the encrypted identifier of the device 102, the device 104 may decrypt it using the static encryption key (event 116). Because the devices 102 and 104 may implement the same symmetric encryption function as well as share the static encryption key, the device 104 thus can obtain the device identifier of the device 102.

Next, the device 104 may encrypt its own device identifier using the shared static encryption key (event 118) and transmit the encrypted device identifier to the device 102 (event 120). The device 102 similarly may decrypt the device identifier of the device 104 using the shared static encryption key (event 122).

At this point, each of the devices 102 and 104 has securely obtained the device identifier of the other device. The devices 102 and 104 now can generate the shared dynamic encryption key. Because the dynamic encryption key includes no time information in this embodiment, a subsequent new communication session between the devices 102 and 104 will produce the same dynamic encryption key. However, a session between another pair of devices, or one of the device 102 and 104 and another device, generally will produce a different dynamic encryption key. Thus, it is believed that generating the dynamic encryption key as discussed is associated with acceptable trade-offs between data security and simplicity of implementation.

With continued reference to FIG. 2, the device 102 may generate the dynamic encryption key using the pair device identifiers and a bitwise XOR function, for example (event 134A). The device 104 similarly may generate the same dynamic encryption key using the same pair of device identifiers and the same bitwise XOR function. In this manner, the devices 102 and 104 can obtain a multi-factor dynamic encryption key substantially unique to the pair of the devices 102 and 104. As an alternative to the XOR function, the devices 102 and 104 can use any suitable algorithm with low latency low computational complexity.

Next, the device 102 may encode a data payload using the dynamic encryption key (event 140) and send the encrypted payload to the device 104 (event 142). The device 104 may use the dynamic encryption key to decrypt the data payload (event 144). Similarly, the device 104 may encode a data payload using the dynamic encryption key (event 146) and send the encrypted payload to the device 102 (event 148). The device 102 similarly may use the dynamic encryption key to decrypt the data payload (event 150).

Figure 3:
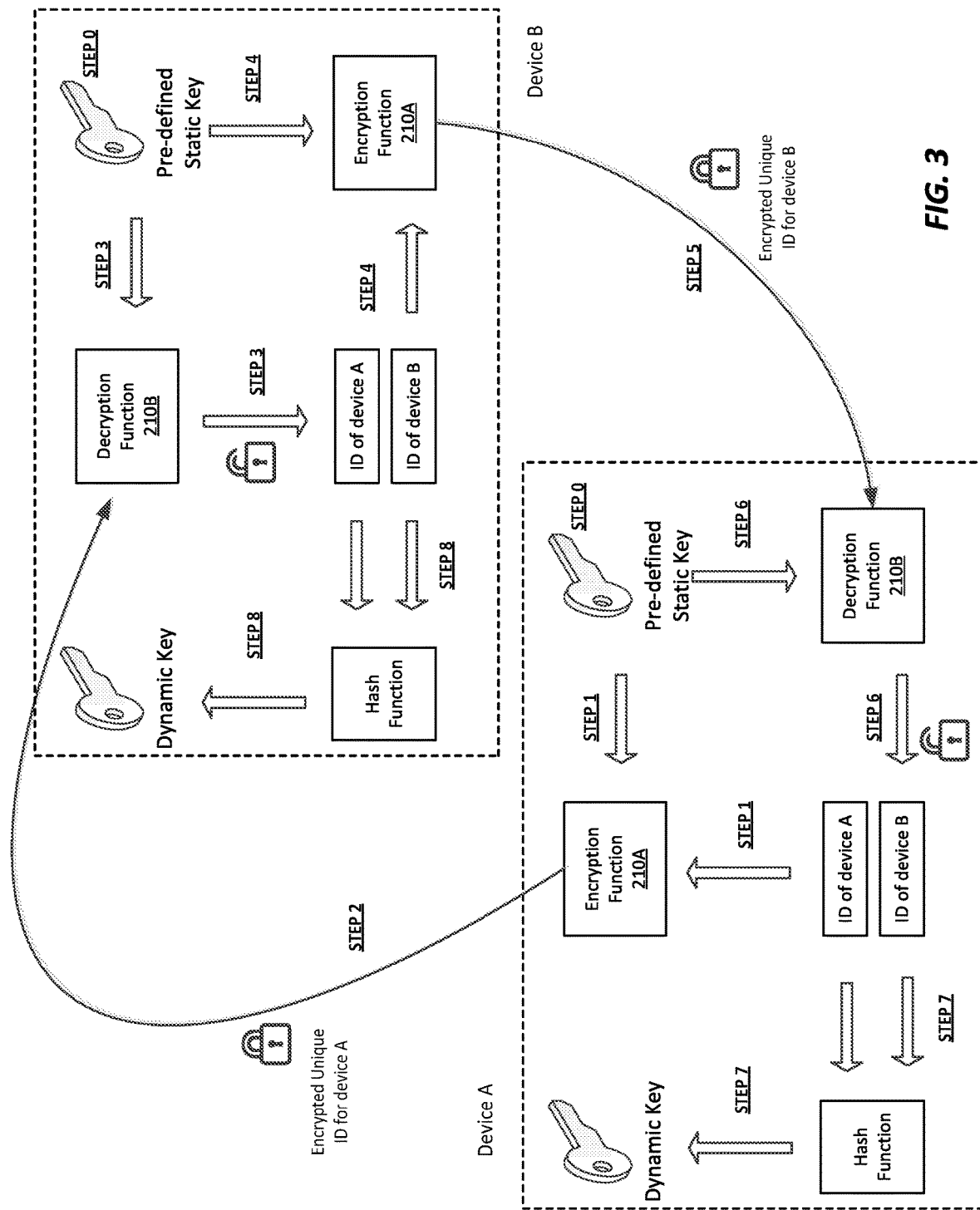
FIG. 3 is a block diagram that schematically illustrates the generation of a dynamic key for exchanging data between a pair of devices, which can be implemented in the system of FIG. 1.

For further clarity, a block diagram 200 in FIG. 3 schematically illustrates a technique for generating a dynamic key for exchanging data between devices A and B. The devices A and B can correspond to the devices 12 and 14, or devices 102 and 104 discussed above, or another pair of communicating devices. Separate blocks in the diagram 200 do not necessarily indicate a physical separation between the corresponding modules. For example, in FIG. 3 encryption and decryption functions are illustrated separately for clarity but may be implemented in the same integrated circuit or same set of instructions.

At step 0, copies of a same share, predefined static key may be loaded into each of the devices A and B. At step 1, which can occur in response to the device A and/or the device B detecting a short-range wireless connection between the devices A and B, the device A may apply the pre-defined static key to the device identifier of the device A using an encryption function 210A. The device A then may send the encrypted device identifier to the device B via a short-range communication link, as step 2. The device identifier of the device A thus can be transmitted to the device B in a secure manner.

At step 3, the device B may apply a decryption function 210B to the received encrypted device identifier. The functions 210A and 210B may implement the same symmetric encryption/decryption scheme. As a result of applying the decryption function 210B, the device B can obtain the device identifier for the device A, as schematically illustrated in FIG. 3.

Step 4 corresponds to the device B encrypting its own device identifier using the shared pre-defined static key. The device B may send the encrypted device identifier to the device A at step 5. The device A then may decrypt the device identifier using the decryption function 210B. It is noted that the devices A and B need not exchange device identifiers encrypted using shared static key sequentially, and in other embodiments steps 1-3 and 4-6 may be carried out in the opposite order or in parallel. In any case, the devices A and B may generate respective copies of the same shared dynamic key using a hash function, at steps 7 and 8. The hash function may implement an XOR operation (dynamic key=device identifier A⊕device identifier B) or simply concatenate the two identifiers according to a pre-defined principle (e.g., lower number first).

Figure 4:
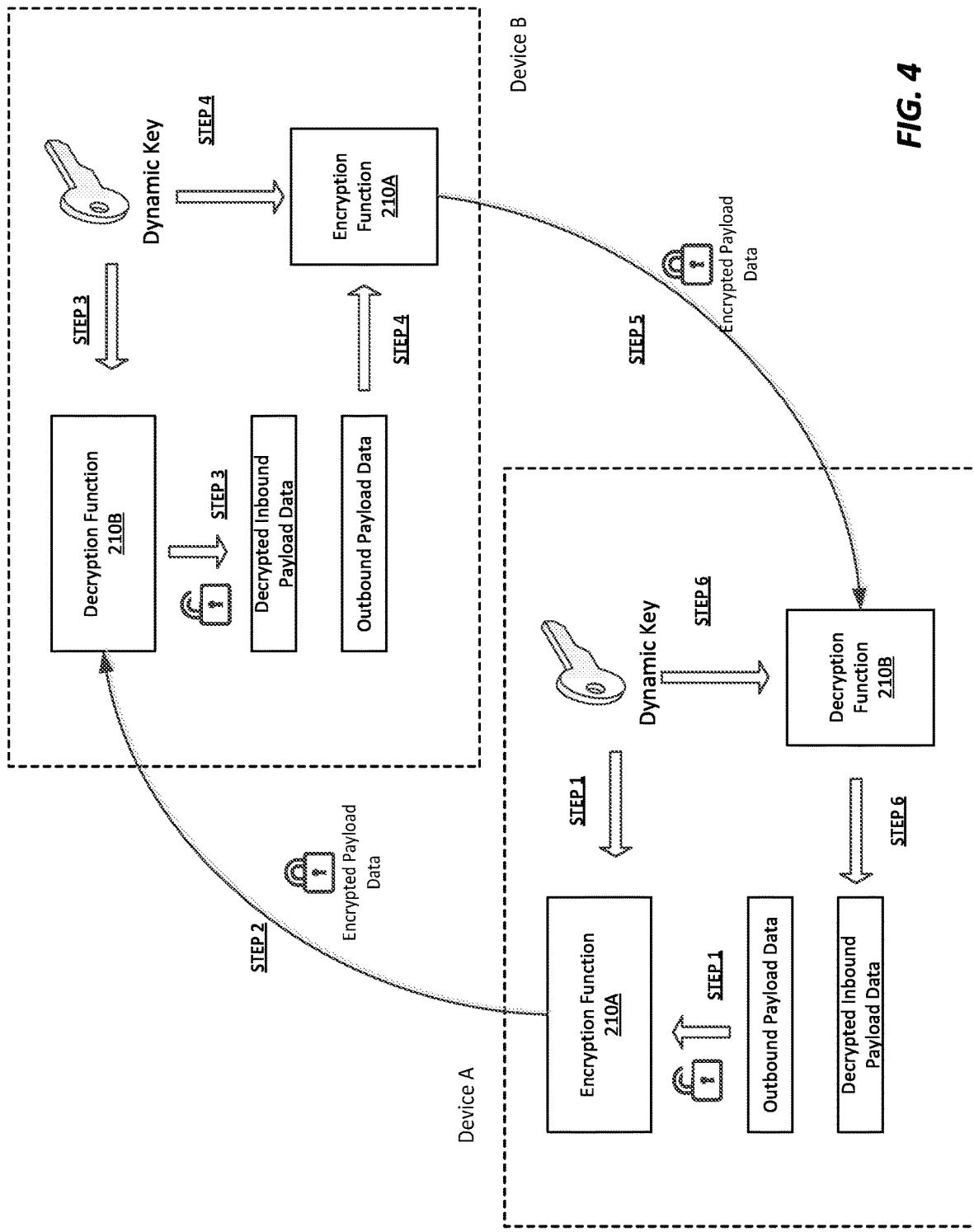
FIG. 4 is a block diagram that schematically illustrates data encryption using the dynamic key generated according to the block diagram of FIG. 3.

Next, a block diagram 250 of FIG. 4 schematically illustrates example data encryption using the dynamic key generated in accordance with the techniques discussed above. At step 1, the device A may encrypt an outbound data payload using the dynamic key. To make implementation easier, the devices A and B may use the same encryption function to encrypt the static key and data payload. In other embodiments, however, the devices A and B apply different encryption functions for these two types of data. For example, the devices A and B can use a more robust encryption function for data payloads.

At step 2, the device A may send the encrypted payload to the device B via the short-range wireless communication link. The device B may decode the received payload using the decryption function 210B and the dynamic key to obtain decrypted inbound payload data at step 3.

At steps 4-6, the device B similarly may provide payload to the device A in a secure manner. In particular, the device B may use the dynamic key and the encryption function 210A to encrypt outbound payload data, at step 4. The device B then may send the encrypted payload data to the device A at step 5. At step 6, the device A may decode the received payload using the decryption function 210B and the dynamic key to obtain decrypted inbound payload data.

Figure 5:
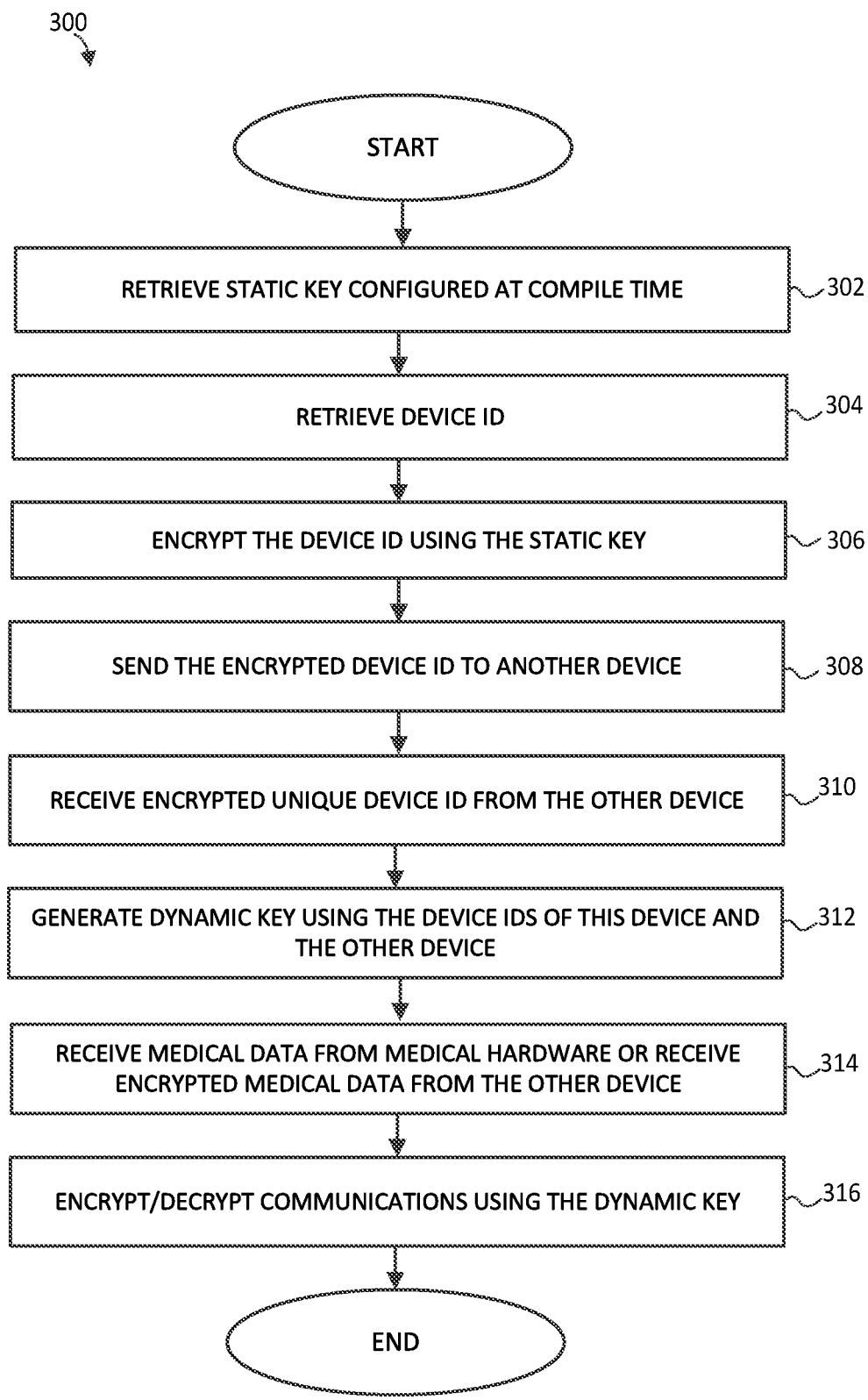
FIG. 5 is a flow diagram of an example method for setting up secure communications, which can be implemented in the system of FIG. 1.

Next, FIG. 5 illustrates a flow diagram of an example method 300, which can be implemented in the medical device 12. A similar method also can be implemented in a non-medical device that communicates with the medical device, such as a remote control device or a smartphone. Depending on the implementation, some of the steps of the method 300 can be implemented using hardware, while other steps can be implemented using firmware and/or software. More generally, the method 300 can be implemented using any suitable combination of hardware, firmware, and software.

The example method 300 begins at block 302, where the medical device is provisioned with a static key at compile time. Alternatively, when the medical device includes a user interface, the user can manually provision the static key. Next, the device identifier is retrieved from the corresponding register at block 304. In some embodiments, the medical device additionally adjusts the size of the device identifier downward or upward in accordance with a pre-defined format.

At block 306, the device identifier is encrypted using the static key and, at block 308, the encrypted device identifier is sent to another device. The encrypted device identifier may be sent using an IEEE 802.11 or IEEE 802.15 protocol, for example.

An encrypted device identifier of the other device is received at block 310. Because the encrypted device identifier is encrypted at the other device using the same shared key, the encrypted device identifier of the other device can be decrypted using the shared key.

Next, at block 312, the device identifier of the medical device is combined with the decrypted device identifier of the other device to generate a dynamic encryption key. The dynamic encryption key is substantially unique to the pair of communicating devices. In other words, the dynamic encryption key is highly unlikely to be reproduced by another pair of communicating devices. Nevertheless, in some embodiments, another pair of devices may generate the same dynamic encryption key if, for example, the bitwise XOR operation is used to combine the device identifiers and each pair of bits in the same position within the device identifiers produces the same result.

At block 314, the medical device receives medical data from the medical hardware operating within the medical device, or the medical device receives encrypted medical data from the other device via the short-range communication link. In the former case, the medical data may include patient data collected using one or several sensors, an indication of successful delivery of a medicament, the status of the medical hardware (i.e., low level of medicine in the syringe), etc. In the latter case the encrypted medical data from the other device may include a command to deliver the medicament using the medical hardware, an indication that an alert should be generated at the medical device, a request for the status of the medical device, etc.

In both cases, the medical device may apply the dynamic key generated at block 312 to the medical data generated at the medical device to encrypt it to the medical data received from the other device to decrypt it.

Drug Information

As mentioned above, the medical devices described herein, including, for example, the medical device 12 and/or the peer device 14, each may be configured as a drug delivery device including at least one container that is filled, partially or entirely, with a drug. This drug may be any one or combination of the drugs listed below, with the caveat that the following list should neither be considered to be all inclusive nor limiting.

For example, the syringe may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the syringe may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1 K; L1C; L1C 1 K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1 D4; AbGC1 E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 14667;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686, 292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GPIIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the drug comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the drug comprises a therapeutically effective amount of the anti-TSLP antibody designated as A5 within U.S. Pat. No. 7,982,016.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the medical devices, systems, methods, and their elements.

What is claimed is:

1. A medical device with limited computational capability, the medical device comprising:
    medical hardware configured to perform a medical function on a human or animal body;
    a first register to store a static, substantially unique identifier of the medical device;
    a second register to store a static encryption key;
    an interface to receive and transmit data over a short-range communication link; and
    processing hardware communicatively coupled to the first register, the second register, the interface and the medical hardware, the processing hardware configured to:
        (i) apply the static encryption key to the identifier of the medical device to generate an encrypted identifier of the medical device,
        (ii) transmit, via the interface, the encrypted identifier of the medical device to another device,
        (iii) receive, via the interface, an encrypted identifier of the other device,
        (iv) decrypt the encrypted identifier of the other device using the static encryption key to determine an identifier of the other device,
        (v) generate a dynamic encryption key using the identifier of the medical device and the identifier of the other device, and
        (vi) apply the dynamic encryption key to medical data transmitted between the medical device and the other device, wherein the medical data is related to operation of the medical hardware.

2. The medical device of claim 1, wherein to generate the dynamic encryption key, the processing hardware is configured to apply a bitwise XOR operation to the identifier of the medical device and the identifier of the other device.

3. The medical device of claim 1, wherein to generate the dynamic encryption key, the processing hardware is configured to concatenate the identifier of the medical device with the identifier of the other device.

4. The medical device of claim 1, wherein each of the medical device and the other device is provisioned with the static encryption key at compile time.

5. The medical device of claim 1, wherein the medical hardware is configured to generate first medical data, and wherein the processing hardware is configured to apply the dynamic encryption key to the first medical data and transmit the encrypted first medical data to the other device.

6. The medical device of claim 5, wherein the processing hardware is configured to (i) apply the dynamic encryption key to encrypted second medical data received from the other device and (ii) provide the decrypted second medical data to the medical hardware, wherein the medical hardware is configured to operate according to the second medical data.

7. The medical device of claim 1, wherein the medical hardware is configured to deliver a medicine into a patient, and wherein the medical data is indicative of a time of delivery.

8. A system comprising:
    a first device including:
        medical hardware configured to perform a medical function on a human or animal body and generate medical data related to the medical function,
        an interface to receive and transmit data over a short-range communication link, and
        processing hardware configured to generate a dynamic encryption key, encrypt the medical data using the dynamic encryption key, and transmit the encrypted medical data via the short-range communication link; the system further comprising:
    a second device including:
        an interface to receive and transmit data over the short-range communication link, and
        processing hardware configured to generate the dynamic encryption key, receive the encrypted medical data via the short-range communication link, and decrypt the medical data using the dynamic encryption key;
    wherein each of the first device and the second device stores a shared static encryption key and a respective different device identifier, and wherein each of the first device and the second device generates the dynamic encryption key using the shared static encryption key and the device identifiers of the first device and the second device.

9. The system of claim 8, wherein the processing hardware of the first device is configured to:
    receive an encrypted device identifier via the short-range communication link, wherein the second device encrypts the device identifier of the second device using the shared static encryption key to generate the encrypted device identifier,
    decrypt the encrypted device identifier using the shared static encryption key, and
    combine the device identifier of the first device with the decrypted device identifier of the second device to generate the dynamic encryption key.

10. The system of claim 9, wherein to combine the device identifier of the first device with the decrypted device identifier of the second device, the processing hardware of the first device is configured to apply a bitwise XOR operation.

11. The system of claim 9, wherein the processing hardware of the first device is further configured to:
encrypt the device identifier of the first device using the shared static encryption key, and
send the encrypted device identifier via the short-range communication link.

12. The system of claim 8, wherein the medical function which the medical hardware of the first device is configured to perform is a first medical function, and wherein the second device further includes medical hardware to perform a second medical function on a human or animal body.

13. The system of claim 8, wherein the processing hardware implements symmetric encryption and decryption.

14. A method for generating dynamic encryption keys in medical devices, the method comprising:
retrieving, by processing hardware, an identifier of a medical device and a pre-stored static key;
receiving, via a short-range wireless communication link, an encrypted identifier of a peer device;
decrypting, by processing hardware, the encrypted identifier using the pre-stored static key to determine an identifier of the peer device;
generating, by processing hardware, a dynamic encryption key using the identifier of a medical device and the identifier of the peer device;
performing a medical function by medical hardware, the medical function being associated with medical data;
exchanging the medical data with the peer device via the wireless communication link, including applying the dynamic encryption key to the medical data.

15. The method of claim 14, wherein generating the dynamic encryption key using the identifier of the medical device and the identifier of the peer device includes combining the identifier of the medical device and the identifier of the peer device using a bitwise XOR operation.

16. The method of claim 14, wherein the medical hardware generates the medical data as output, and wherein exchanging the medical data with the peer device includes:
encrypting the medical data using the dynamic encryption key, and
sending encrypted medical data to the peer device.

17. The method of claim 14, wherein the medical data includes a command for operating the medical hardware, and wherein exchanging the medical data with the peer device includes:
receiving encrypted medical data from the peer device,
decrypting the encrypted medical data using the dynamic encryption key, and
applying the command included in the medical data to the medical hardware.

18. The method of claim 14, wherein exchanging the medical data with the peer device includes:
receiving encrypted first medical data from the peer device;
decrypting the encrypted first medical data using the dynamic encryption key;
encrypting second medical data generated by the medical hardware using the dynamic encryption key, and
sending the encrypted second medical data to the peer device.

19. The method of claim 18, wherein decrypting the encrypted first medical data and encrypting the second medical data includes using a same symmetric encryption function.

20. The method of claim 14, further comprising:
applying, by processing hardware, the static key to the identifier of the medical device to generate an encrypted identifier of the medical device; and
transmitting the encrypted identifier of the medical device to the peer device via the short-range wireless communication link.

* * * * *

UNITED STATES PATENT AND TRADEMARK OFFICE
CERTIFICATE OF CORRECTION

| | |
|---|---|
| PATENT NO. | : 11,238,150 B2 |
| APPLICATION NO. | : 16/300705 |
| DATED | : February 1, 2022 |
| INVENTOR(S) | : Huaying Yang et al. |

It is certified that error appears in the above-identified patent and that said Letters Patent is hereby corrected as shown below:

On the Title Page

At page 2, in Column 1, item (57), under "ABSTRACT", Line 2, "identifier of to" should be -- identifier to --.

In the Claims

At Column 24, Line 24, In Claim 18, "key, and" should be -- key; and --.

Signed and Sealed this
Thirteenth Day of December, 2022

Katherine Kelly Vidal
*Director of the United States Patent and Trademark Office*